United States Patent
Nakamura et al.

(10) Patent No.: US 6,705,772 B2
(45) Date of Patent: Mar. 16, 2004

(54) OPTICAL FIBER SPLICING METHOD AND OPTICAL FIBER

(75) Inventors: Motonori Nakamura, Yokohama (JP); Osamu Kasuu, Yokohama (JP); Daisuke Yokota, Yokohama (JP); Yuichi Ohga, Yokohama (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 62 days.

(21) Appl. No.: 10/161,624

(22) Filed: Jun. 5, 2002

(65) Prior Publication Data

US 2002/0181904 A1 Dec. 5, 2002

(30) Foreign Application Priority Data

Jun. 5, 2001 (JP) ........................................ 2001-169929

(51) Int. Cl.[7] .............................................. G02B 6/255
(52) U.S. Cl. .............................. 385/96; 385/97; 385/98; 65/407; 219/383
(58) Field of Search ............................. 385/95, 96, 97, 385/98; 65/407, 429; 219/383, 384

(56) References Cited

U.S. PATENT DOCUMENTS 6,294,760 B1 * 9/2001 Inoue et al. ............... 385/97 X
6,550,985 B2 * 4/2003 Nakamura et al. ............ 385/96
6,553,791 B1 * 4/2003 Osaka et al. .................. 65/407

FOREIGN PATENT DOCUMENTS

JP  05-215931  8/1993
JP  07-248423  9/1995

* cited by examiner

Primary Examiner—Phan T. H. Palmer
(74) Attorney, Agent, or Firm—McDermott, Will & Emery

(57) ABSTRACT

An optical fiber splicing method capable of fully reducing the splice loss at room temperature is provided. In the optical fiber splicing method in accordance with the present invention, respective end faces of optical fibers are fused together in a splicing step (S101). In a condition setting step (S102), a set value $\alpha_0$ is set. Thereafter, a heating step (S103), a measuring step (S104), and a termination determining step (S105) are carried out repeatedly. In the heating step, a region including the fusion-spliced point is heated under a predetermined heating condition. In the measuring step, splice loss is measured. In the termination determining step, the splice loss $\alpha_n$ measured in the measuring step and the set value $\alpha_0$ set in the condition setting step are compared with each other in terms of magnitude. If the splice loss $\alpha_n$ is not greater than the set value $\alpha_0$, then it is determined that the alternation should be terminated, whereby the optical fiber connecting operation is terminated.

21 Claims, 14 Drawing Sheets

OPTICAL FIBER SPLICING METHOD AND OPTICAL FIBER

BACKGROUND OF THE INVENTION

1. Field of the Invention

The present invention relates to an optical fiber splicing method in which respective end faces of first and second optical fibers are fused and spliced to each other, and an optical fiber made by this method.

2. Related Background Art

Known as methods of connecting first and second optical fibers to each other are connector connection and fusion splicing. The fusion splicing, in which respective end faces of the first and second optical fibers are fused and spliced to each other, yields a lower splice loss and higher reliability than the connector connection does. Therefore, the fusion splicing is employed more often in general. In the case where the first and second optical fibers have respective mode-field diameters different from each other (e.g., one of them is a single-mode optical fiber whereas the other is a dispersion-compensating optical fiber) or in the case where the mode-field diameter of one of the first and second optical fibers is locally changed upon fusion, however, the splice loss therebetween is not sufficiently low.

Therefore, in the heating step after the splicing step, the dopant added to each optical fiber has been diffused, so as to lower the difference between mode-field diameters of the first and second optical fibers at their fusion-spliced part, or reduce the change in mode field diameter between the first and second optical fibers at their fusion-spliced part, thereby lowering the splice loss. Japanese Patent Application Laid-Open No. HEI 5-215931 and No. HEI 7-248423, for example, disclose that, in the case where the splice loss is measured simultaneously with the heating step, and the heating step is terminated at the time when thus measured splice loss becomes a predetermined value or less, the splice loss can reliably be reduced to a predetermined value or less.

SUMMARY OF THE INVENTION

However, the inventor has found that there is a case where the splice loss cannot be reduced to a predetermined value or less by the method disclosed in the above-mentioned publications. Namely, even if the heating step is terminated immediately after the measured splice loss attains a predetermined value or less, the splice loss measured upon heating immediately before the termination and the splice loss measured at room temperature after the termination will not always coincide with each other. Such a disparity is presumed to occur because of the fact that the thermal vibration of elements constituting each optical fiber at the time of heating differs from that at room temperature, so that the refractive index varies, thereby yielding mode field diameters different from each other. Due to such a disparity, the splice loss at room temperature is hard to decrease sufficiently.

In order to overcome the above-mentioned problem according to such inventor's findings, it is an object of the present invention to provide an optical fiber splicing method and an optical fiber which can fully reduce the splice loss at room temperature.

The optical fiber splicing method in accordance with the present invention is a method of splicing a first optical fiber and a second optical fiber to each other by fusing respective end faces thereof, the method comprising (1) a splicing step of fusing the respective end faces of the first and second optical fibers and splicing them; (2) a heating step of heating a region including a fusion-spliced part between the first and second optical fibers fused in the splicing step; (3) a measuring step, alternately carried out with the heating step, of measuring a splice loss between the first and second optical fibers fused in the splicing step; and (4) a termination determining step of determining, according to a splice loss value measured in the measuring step, whether or not to terminate alternation of the heating and measuring steps. In the optical fiber splicing method in accordance with the present invention, the alternation is terminated when it is determined in the termination determining step that the alternation should be terminated.

In the present invention, whether or not to terminate the alternation of heating and measuring steps is determined according to the splice loss value measured in the measuring step. If it is resultantly determined that the alternation should be terminated, then the alternation is terminated, whereby the optical fiber connecting operation is terminated. As a consequence, the splice loss at room temperature is fully reduced.

In the optical fiber splicing method in accordance with the present invention, it may be determined in the termination determining step that the alternation should be terminated if the splice loss measured in the measuring step becomes a set value or less. Alternatively, it may be determined in the termination determining step that the alternation should be terminated if the difference between the splice loss measured in the measuring step and that at a previous measuring time becomes a set value or smaller.

In the optical fiber splicing method in accordance with the present invention, the termination determining step may be performed within a range of only a predetermined number of the alternation. This is suitable in cases where there are a plurality of values of number n of alternation at which the splice loss attains minimum values.

In the optical fiber splicing method in accordance with the present invention, a heating time in the first heating step may be made longer than that in the second and later heating steps. In this case, a desirable splice loss can be attained in a short time in total.

The optical fiber splicing method in accordance with the present invention may further comprise a change determining step of determining, according to the splice loss value measured in the measuring step, whether or not to change a heating condition in the heating step thereafter, and may change the heating condition in the heating step thereafter when it is determined in the change determining step that the heating condition should be changed.

In the optical fiber splicing method in accordance with the present invention, it may be determined in the change determining step that the heating condition should be changed if the splice loss measured in the measuring step becomes a set value or less. Alternatively, it may be determined in the change determining step that the heating condition should be changed if the difference between the splice loss measured in the measuring step and that at a previous measuring time becomes a set value or smaller.

In the optical fiber splicing method in accordance with the present invention, the change determining step may be performed within a range of only a predetermined number. This is suitable in cases where there are a plurality of values of number n of alternation at which the splice loss attains the minimum value.

In the optical fiber splicing method in accordance with the present invention, it may be determined in a plurality of change determining steps that the heating condition should be changed.

Preferably, in the optical fiber splicing method in accordance with the present invention, when it is determined in the change determining step that the heating condition should be changed, a heating temperature is lowered in the heating step thereafter, a heating time is shortened in the heating step thereafter, or a heating temperature is lowered while a heating time is shortened in the heating step thereafter.

The optical fiber splicing method in accordance with the present invention may further comprise an annealing step of cooling the fusion-spliced part to a temperature of 200° C. over a period of at least 10 seconds after it is determined in the termination determining step that the alternation of the heating and measuring steps should be terminated and thus is terminated.

The optical fiber splicing method in accordance with the present invention may further comprise a thermal stress removal step of eliminating a thermal distortion by heat-treating a region including the fusion-spliced part at a predetermined temperature of at least 500° C. but not higher than 1200° C. while being lower than the heating temperature in the heating step after it is determined in the termination determining step that the alternation of the heating and measuring steps should be terminated and thus is terminated, and an annealing step of cooling the fusion-spliced part from the predetermined temperature to a temperature of 200° C. over a period of at least 2 seconds after the thermal stress removal step.

In the optical fiber splicing method in accordance with the present invention, a region including the fusion-spliced part may be heat-treated in the annealing step.

In the optical fiber splicing method in accordance with the present invention, a region including the fusion-spliced part may be heat-treated in the thermal stress removal step while a heating source is relatively moved in a longitudinal direction of two optical fibers.

In the optical fiber splicing method in accordance with the present invention, the two optical fibers have a longitudinal temperature gradient of 500° C./mm or less in the thermal stress removal step.

The optical fiber in accordance with the present invention is made by any of the optical fiber splicing methods mentioned above.

DESCRIPTION OF THE PREFERRED EMBODIMENTS

Figure 1:
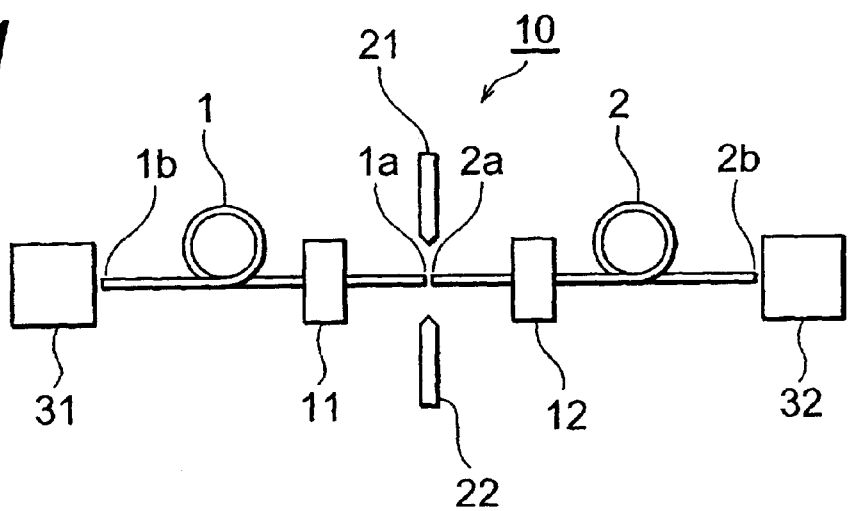
FIG. 1 is a schematic diagram of an optical fiber connecting apparatus 10.

In the following, embodiments of the present invention will be explained in detail with reference to the accompanying drawings. In the explanation of the drawings, constituents identical to each other will be referred to with numerals identical to each other without repeating their overlapping descriptions.

The schematic configuration of an optical fiber connecting apparatus 10 to which optical fiber splicing methods in accordance with embodiments are applied will be explained. The optical fiber connecting apparatus 10 shown in FIG. 1 comprises holding sections 11, 12, heating sources 21, 22, a light source section 31, and a light-receiving section 32.

The holding section 11 holds a first optical fiber 1, whereas the holding section 12 holds a second optical fiber 2. One end face 1a of the optical fiber 1 and one end face 2a of the optical fiber 2 oppose each other. The light source section 31 is connected to the other end face 1b of the optical fiber 1, whereas the light-receiving section 32 is connected to the other end face 2b of the optical fiber 2. As a consequence, light outputted from the light source section 31 is made incident on the other end face 1b of the optical fiber 1, whereas light emitted from the other end face 2b of the optical fiber 2 is received by the light-receiving section 32. Each of the first optical fiber 1 and second optical fiber 2 may be any of single-mode optical fibers, dispersion-compensating optical fibers, dispersion-shifted optical fibers, optical fibers doped with rare-earth elements, and the like.

In a splicing step, the end face 1a of the optical fiber 1 and the end face 2a of the optical fiber 2 are spliced to each other upon being heated/fused by the heating sources 21, 22. The heating sources 21, 22 used in the splicing step are a pair of electrodes disposed so as to hold the fusion-spliced part therebetween. The end face 1a of the optical fiber 1 and the end face 2a of the optical fiber 2 are fusion-spliced to each other by arc discharge between the pair of electrodes.

In a heating step carried out after the splicing step, a region including the fusion-spliced part between the optical fibers 1, 2 fused in the splicing step is heated. As a consequence, dopants added to the optical fibers 1, 2 are diffused, whereby the respective mode-field diameters of the optical fibers 1, 2 at their fusion-spliced part change, thereby altering the splice loss. The heating sources 21, 22 used in this heating step may be a pair of electrodes as mentioned above, or burners or heaters.

A measuring step of measuring the splice loss between the optical fibers 1, 2 fused in the splicing step is carried out alternately with the heating step. Namely, the heating step is not carried out while the splice loss is being measured in the measuring step, whereby each optical fiber is at room temperature. No measurement of splice loss is necessary during when a region including the fusion-spliced part between the optical fibers 1, 2 is heated in the heating step. For measuring the splice loss, light having a constant intensity is made incident on the end face 1b of the optical fiber 1 from the light source section 31, and the intensity of light emitted from the end face 2b of the optical fiber 2 at that time is detected by the light-receiving section 32.

Figure 2:
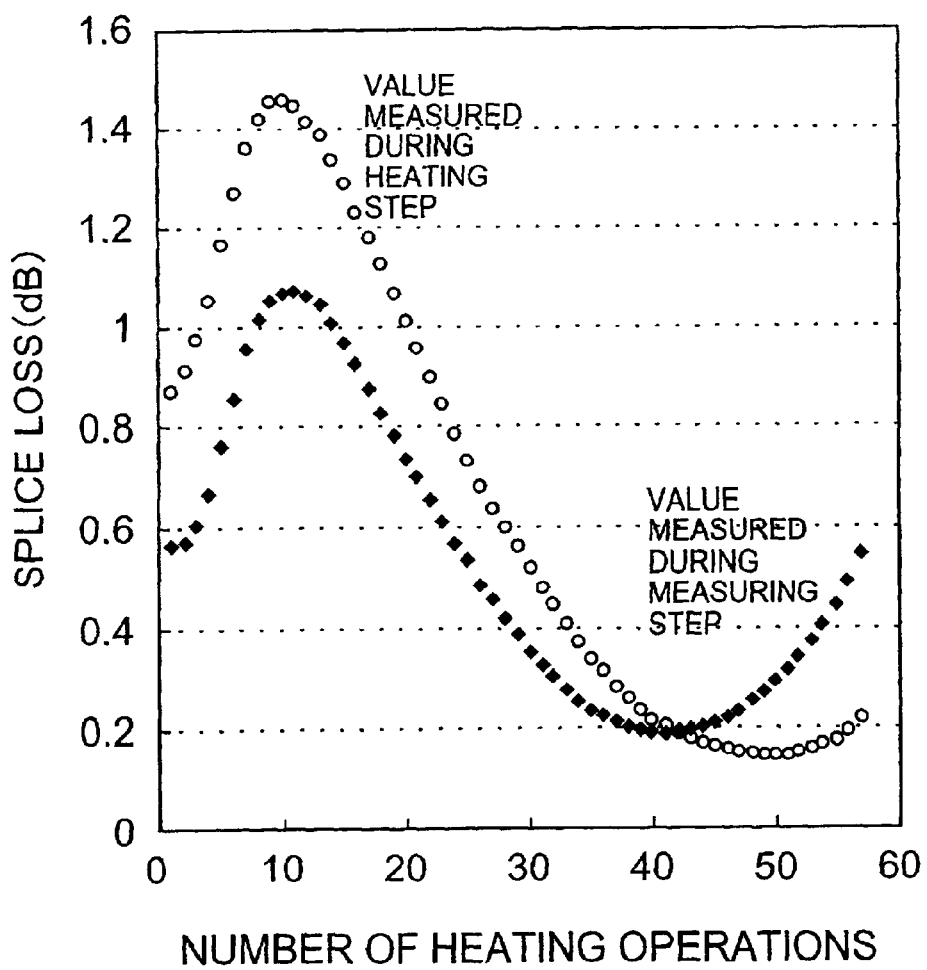
FIG. 2 is a graph showing how splice loss changes when heating and measuring steps were alternately carried out under a constant condition after a splicing step.

FIG. 2 is a graph showing how the splice loss changes when the heating and measuring steps were alternately carried out under a constant condition after the splicing step by using the optical fiber connecting apparatus 10 shown in FIG. 1. The heating time and heating temperature were set constant among the heating steps. The splice loss was measured not only in each measuring step but also during each heating step. As shown in this graph, the splice loss measured during the heating steps became the lowest in about the 50th heating step. On the other hand, the splice loss measured during the measuring steps became the lowest before and after about the 40th heating step. As can be seen from FIG. 2, if the heating step is terminated at the time when the splice loss measured in the heating step attains the lowest value of 0.15 dB as in conventional cases, the splice loss at room temperature after the termination will be 0.3 dB which is twice as high as the former value. The present invention is based on such inventor's findings.

First Embodiment

Figure 3:
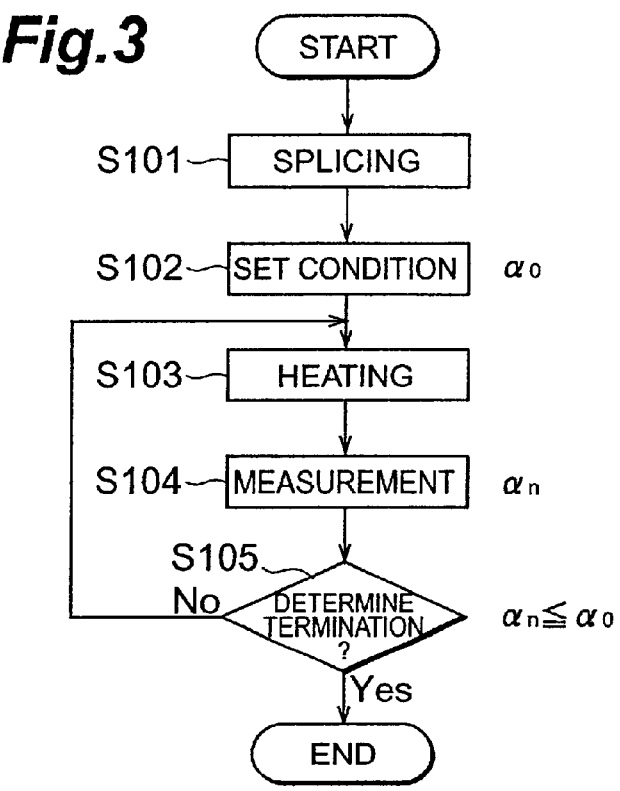
FIG. 3 is a flowchart for explaining the optical fiber splicing method in accordance with a first embodiment.

A first embodiment of the optical fiber splicing method in accordance with the present invention will be explained with reference to FIG. 3. The optical fiber splicing method in accordance with the first embodiment includes a splicing step (S101), a condition setting step (S102), a heating step (S103), a measuring step (S104), and a termination determining step (S105).

In the splicing step (S101), respective end faces of the first and second optical fibers are fused. In its subsequent condition setting step (S102), a set value $\alpha_0$ employed in the termination determining step (S105), which will be carried out later, is set. Then, the heating step (S103), measuring step (S104), and termination determining step (S105) are carried out repeatedly.

In the heating step (S103), a region including the fusion-spliced part between the first and second optical fibers fused in the splicing step (S101) is heated under a constant heating condition. In its subsequent measuring step (S104), the splice loss between the first and second optical fibers fused in the splicing step (S101) is measured. The value of splice loss measured in the n-th measuring step (S104) is defined as $\alpha_n$.

In the termination determining step (S105), the splice loss $\alpha_n$ measured in the measuring step (S104) and the set value $\alpha_0$ set in the condition setting step (S102) are compared with each other in terms of magnitude, whereby it is determined whether the alternation of the heating step (S103) and measuring step (S104) should be terminated or not. If the splice loss $\alpha_n$ is not greater than the set value $\alpha_0$, then it is determined that the alternation should be terminated, whereby the optical fiber connecting operation is terminated. If the splice loss $\alpha_n$ exceeds the set value $\alpha_0$, then the flow returns to the previous heating step (S103) in order to continue the alternation.

In the optical fiber splicing method in accordance with this embodiment, as in the foregoing, the heating and measuring steps are carried out alternately, so that the splice loss is measured when each optical fiber is not heated, and the optical fiber connecting operation is terminated when thus measured splice loss is not greater than the set value. As a consequence, the value of splice loss measured in the measuring step becomes one obtained in an environment used in practice, whereby the splice loss at room temperature is fully reduced.

Specific Example 1 of the optical fiber splicing method in accordance with the first embodiment will now be explained. In this example, a single-mode optical fiber was used as the first optical fiber, whereas a dispersion-compensating optical fiber was used as the second optical fiber. Arc discharge was used in the splicing step, whereas the splice loss after the splicing step was 1.10 dB. A burner was used in the heating step, whereas a mixed gas composed of a propane gas (with a feed rate of 20 cc/min) and an oxygen gas (with a feed rate of 30 cc/min) was supplied to the burner. In each heating step, heating was carried out for 20 seconds. The time interval between one heating step and the next heating step was 10 seconds, during which the measuring step and termination determining step were carried out. The set value $\alpha_0$ was 0.20 dB. The heating, measuring, and termination determining steps were repeatedly carried out until the measured splice loss $\alpha_n$ became the set value $\alpha_0$ or less. As a result, the measured splice loss $\alpha_n$ became the set value $\alpha_0$ or less at the time when the number n of alternation reached 32, whereby the optical fiber connecting operation was terminated. The time required after terminating the condition setting step was 950 seconds.

Second Embodiment

Figure 4:
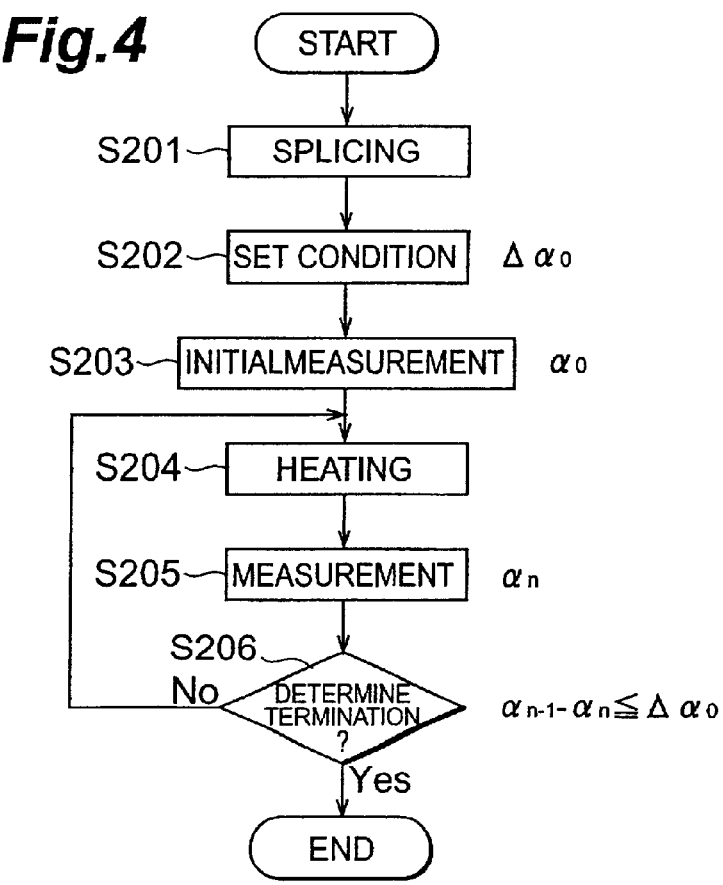
FIG. 4 is a flowchart for explaining the optical fiber splicing method in accordance with a second embodiment.

A second embodiment of the optical fiber splicing method in accordance with the present invention will now be explained with reference to FIG. 4. The optical fiber splicing method in accordance with the second embodiment includes a splicing step (S201), a condition setting step (S202), an initial measurement step (S203), a heating step (S204), a measuring step (S205), and a termination determining step (S206).

The splicing step (S201) is similar to S101 in the first embodiment. In its subsequent condition setting step (S202), a set value $\Delta\alpha_0$ used in the termination determining step (S206), which will be carried out later, is set. In the initial measurement step (S203), the splice loss $\alpha_0$ between the first and second optical fibers fused in the splicing step (S201) is measured. Thereafter, the heating step (S204), measuring step (S205), and termination determining step (S206) are carried out repeatedly.

In the termination determining step (S206), the difference $\Delta\alpha_n$ ($=\alpha_{n-1}-\alpha_n$) between the splice loss $\alpha_n$ measured in the n-th measuring step (S205) and the splice loss $\alpha_{n-1}$ measured in its previous measuring step (S205) is determined. At the first time (n=1), the difference $\Delta\alpha_1$ ($=\alpha_0-\alpha_1$) between the splice loss $\alpha_1$ measured in the first measuring step (S205) and the splice loss $\alpha_0$ measured in the initial measurement step (S203) is determined. According to the value of this difference $\Delta\alpha_n$, it is determined whether to terminate the alternation of the heating step (S204) and measuring step (S205) or not. If the difference $\Delta\alpha_n$ is not greater than the set value $\Delta\alpha_0$, then it is determined that the alternation should be terminated, whereby the optical fiber connecting operation is terminated. If the difference $\Delta\alpha_n$ exceeds the set value $\Delta\alpha_0$, then the flow returns to the previous heating step (S204) in order to continue the alternation.

The optical fiber splicing method in accordance with this embodiment utilizes the fact that the splice loss decreasing rate becomes lower in the vicinity of the number n of operations at which the splice loss attains a minimal value, whereby the above-mentioned difference $\Delta\alpha_n$ has a smaller value. When the value of the above-mentioned difference $\Delta\alpha_n$ is not greater than the set value $\Delta\alpha_0$, it is considered that the number of operations has reached near the number n at which the splice loss attains a minimal value, whereby it is determined that the above-mentioned alternation should be terminated.

In the optical fiber splicing method in accordance with this embodiment, the value of splice loss measured in the measuring step becomes one obtained in an environment used in practice, whereby the splice loss at room temperature is fully reduced.

Specific Example 2-1 of the optical fiber splicing method in accordance with the second embodiment will now be explained. The optical fiber, arc discharge, burner, mixed gas, each heating time, and times of the measuring and termination determining steps used in this example are the same as those in Example 1. The set value $\Delta\alpha_0$ was 0.01 dB. Then, the heating, measuring, and termination determining steps were repeated until the measured difference $\Delta\alpha_n$ became the set value $\Delta\alpha_0$ or less. As a result, the measured difference $\Delta\alpha_n$ became the set value $\Delta\alpha_0$ or less at the time when the number n of alternation reached 33, whereby the optical fiber connecting operation was terminated. The time required after terminating the condition setting step was 980 seconds. The finally obtained splice loss $\alpha_{33}$ was 0.19 dB.

Example 2-2 was the same as Example 2-1 except that dispersion-compensating optical fibers of the same kind were used as the first and second optical fibers. The splice loss $\alpha_0$ obtained in the initial measurement step was 0.90 dB. The measured difference $\Delta\alpha_n$ became the set value $\Delta\alpha_0$ or less when the number n of alternation became 4, whereby the optical fiber splicing method was terminated. The time required after terminating the condition setting step was 110 seconds. The finally obtained splice loss $\alpha_4$ was 0.17 dB.

Third Embodiment

Figure 5:
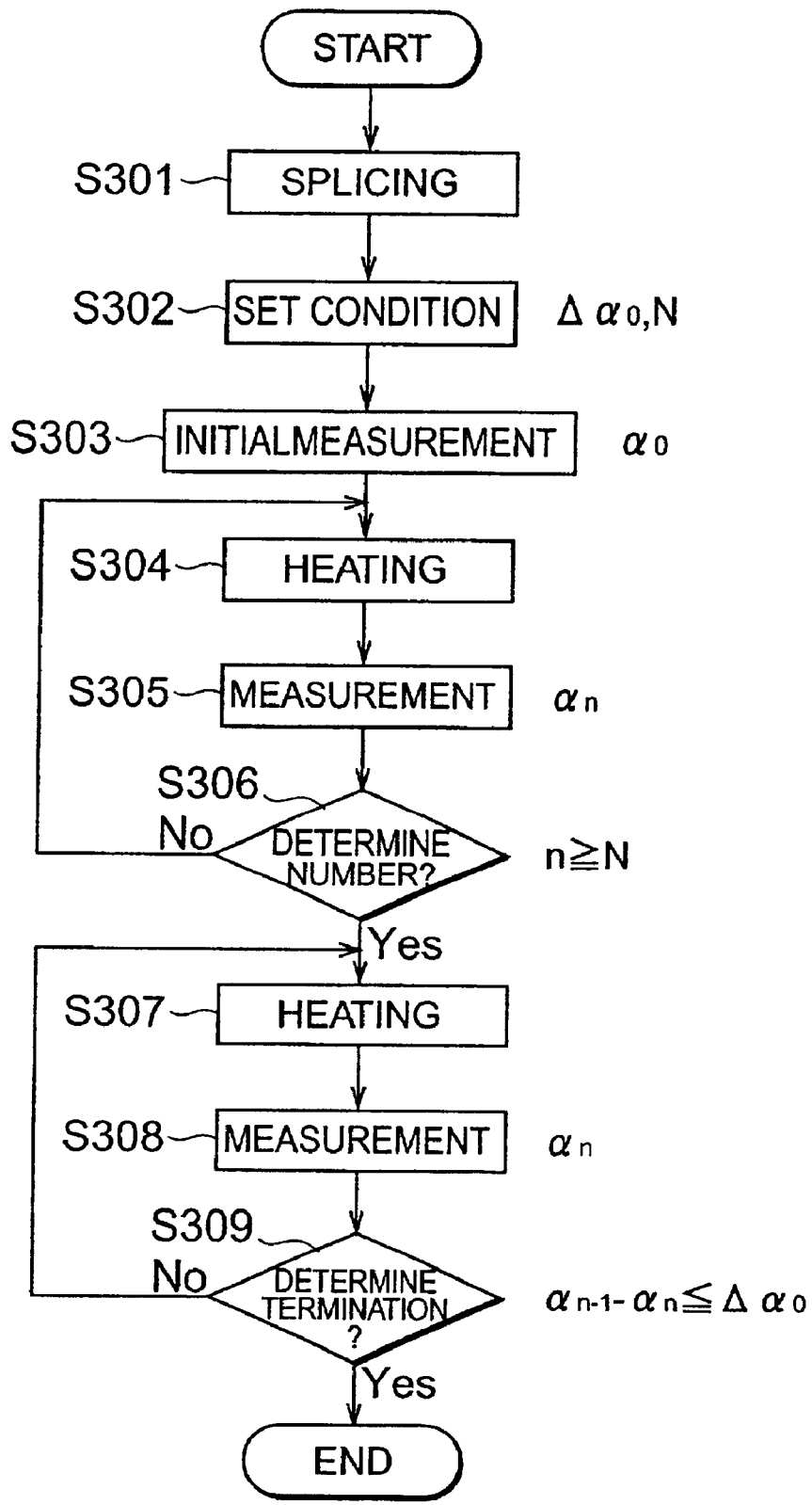
FIG. 5 is a flowchart for explaining the optical fiber splicing method in accordance with a third embodiment.

A third embodiment of the optical fiber splicing method in accordance with the present invention will now be explained with reference to FIG. 5. The optical fiber splicing method in accordance with the third embodiment includes a splicing step (S301), a condition setting step (S302), an initial measurement step (S303), an earlier heating step (S304), an earlier measuring step (S305), a number determining step (S306), a later heating step (S307), a later measuring step (S308), and a termination determining step (S309).

The heating step (S301) is similar to S101 in the first embodiment. In its subsequent condition setting step (S302), a set value $\Delta\alpha_0$ used in the termination determining step, which will be carried out later, and a set value N used in the number determining step (S306), which will be carried out later, are set. The initial measurement step (S303) is similar to S203 in the second embodiment.

Thereafter, the earlier heating step (S304), earlier measuring step (S305), and number determining step (S306) are repeatedly carried out until it is determined in the number determining step that the number n of alternation has reached N. Then, the later heating step (S307), later measuring step (S308), and termination determining step (S309) are repeatedly carried out until it is determined in the termination determining step that they should be terminated.

Each of the earlier heating step (S304) and later heating step (S307) is similar to S103 in the first embodiment. Each of the earlier measuring step (S305) and later measuring step (S308) is similar to S104 in the first embodiment. The value of splice loss measured in the n-th (where n≧N) measuring step (S308) throughout the earlier and later steps is defined as $\alpha_n$.

The termination determining step (S309) is similar to S206 in the second embodiment. If the difference $\Delta\alpha_n$ exceeds the set value $\Delta\alpha_0$, then the flow returns to the previous heating step (S307) in order to continue the above-mentioned alternation.

The optical fiber splicing method in accordance with this embodiment fully reduces the splice loss at room temperature as with the optical fiber splicing method in accordance with the second embodiment.

Since the number determining step (S306) is provided, the optical fiber splicing method in accordance with this embodiment is favorable in cases where there are a plurality of values of the number n of alternation at which the splice loss attains minimal values. Namely, the splice loss at room temperature is fully reduced when the above-mentioned termination determining step is carried out only within a range including an n value at which the splice loss attains the lowest value (or a sufficiently small minimum value if not the lowest value) in these plurality of n values.

Fourth Embodiment

Figure 6:
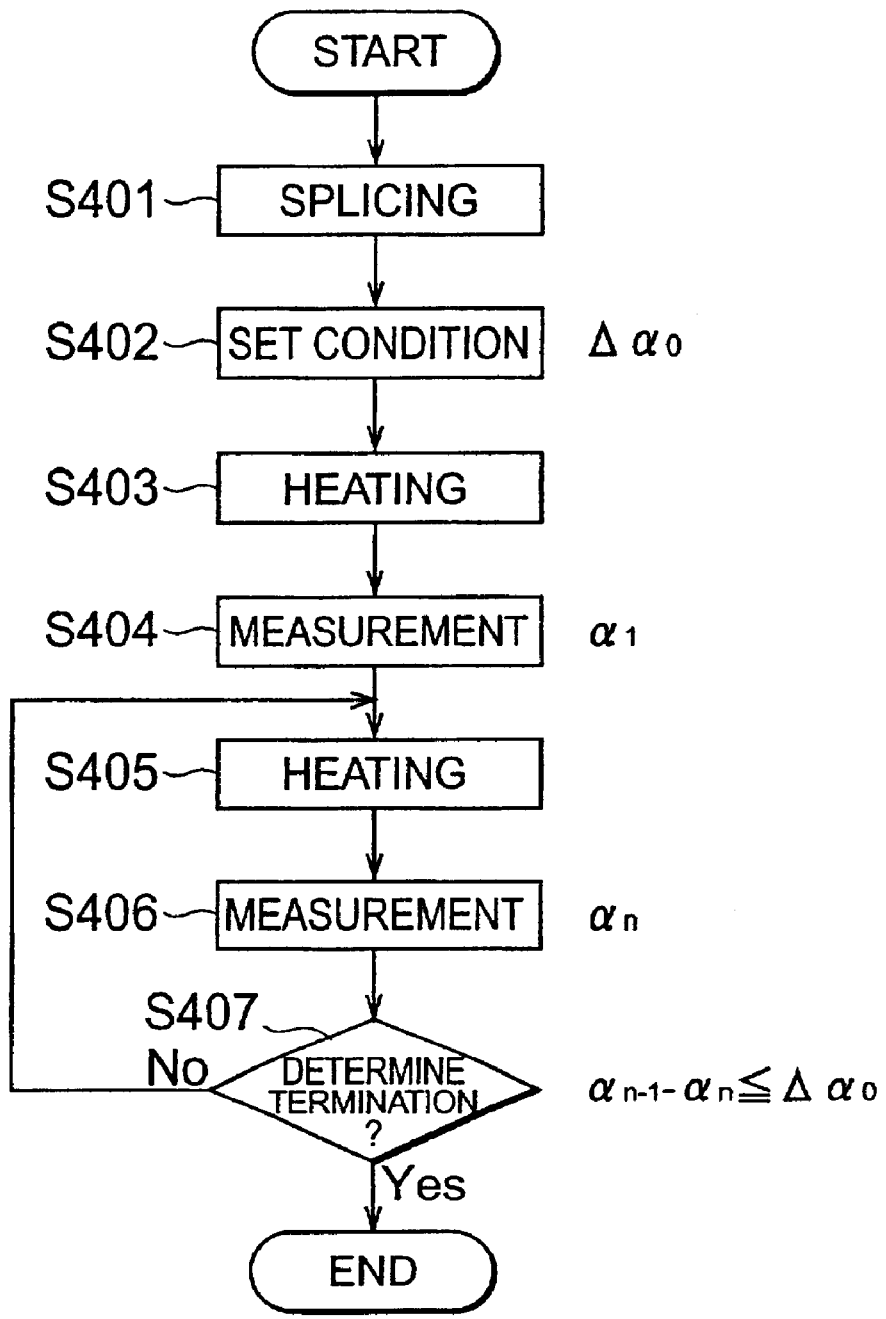
FIG. 6 is a flowchart for explaining the optical fiber splicing method in accordance with a fourth embodiment.

A fourth embodiment of the optical fiber splicing method in accordance with the present invention will now be explained with reference to FIG. 6. The optical fiber splicing method in accordance with the fourth embodiment includes a splicing step (S401), a condition setting step (S402), a first heating step (S403), a first measuring step (S404), a heating step (S405), a measuring step (S406), and a termination determining step (S407).

The splicing step (S401) is similar to S101 in the first embodiment. In its subsequent condition setting step (S402), a set value $\Delta\alpha_0$ used in the termination determining step (S407), which will be carried out later, is set. Then, the first heating step (S403) and first measuring step (S404) are carried out and, thereafter, the heating step (S405), measuring step (S406), and termination determining step (S407) are repeatedly carried out.

Each of the first heating step (S403) and the second and later heating steps (S405) is similar to S103 in the first embodiment. However, the first heating step is carried out for a period of time longer than each of the second and later heating steps. The heating time in the first heating step is shorter than the time at which the splice loss at room temperature attains the lowest value (or a sufficiently small minimum value if not the lowest value). Each of the first measuring step (S404) and the second and later measuring steps (S406) is similar to S104 in the first embodiment.

The termination determining step (S407) is similar to S206 in the second embodiment. If the difference $\Delta\alpha_n$ exceeds the set value $\Delta\alpha_0$, then the flow returns to the previous heating step (S405) in order to continue the above-mentioned alternation.

As in the foregoing, the optical fiber splicing method in accordance with this embodiment fully reduces the splice loss at room temperature as with the optical fiber splicing method in accordance with the above-mentioned second embodiment.

Also, the optical fiber splicing method in accordance with this embodiment can attain a desirable splice loss in a short period of time as a whole, since the first heating step is continuously carried out over a relatively long period of time.

Specific Example 4 of the optical fiber splicing method in accordance with the fourth embodiment will now be explained. The optical fibers, arc discharge, burner, and mixed gas used in this example are the same as those in Example 1. Heating was continuously carried out over a period of 500 seconds in the first heating step, and was carried out for 20 seconds in each of the second and later heating steps. The time interval between one heating step and the next heating step was 10 seconds, during which the measuring step and termination determining step were carried out. The set value $\Delta\alpha_0$ was 0.01 dB. The heating, measuring, and termination determining steps were repeatedly carried out until the measured difference $\Delta\alpha_n$ became the set value $\Delta\alpha_0$ or less. As a result, the measured difference $\Delta\alpha_n$ became the set value $\Delta\alpha_0$ or less at the time when the number n of alternation (each including the first heating step) reached 5, whereby the optical fiber connecting operation was terminated. The time required after terminating the condition setting step was 610 seconds. The finally obtained splice loss $\alpha_5$ was 0.19 dB.

Fifth Embodiment

Figure 7:
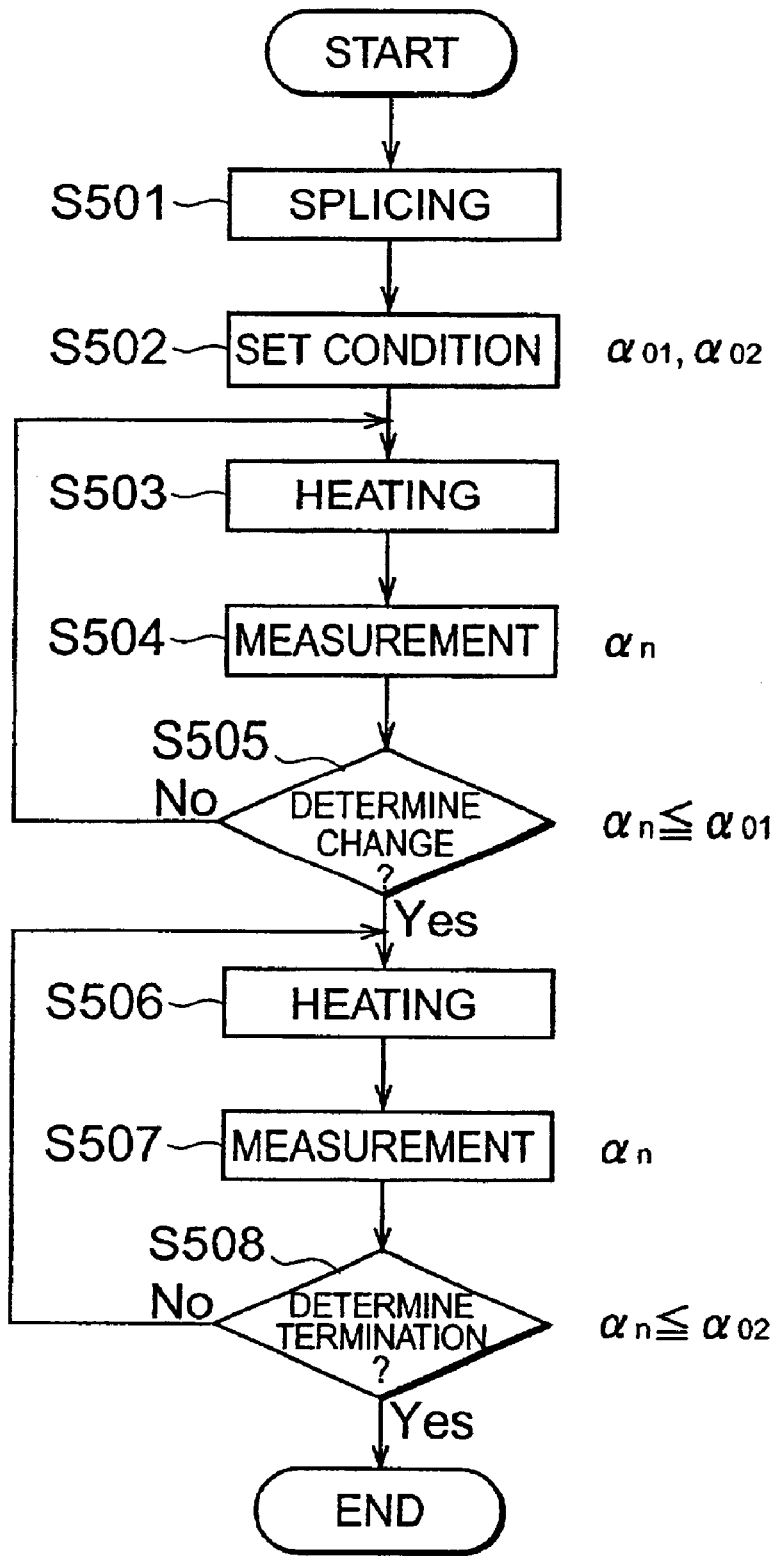
FIG. 7 is a flowchart for explaining the optical fiber splicing method in accordance with a fifth embodiment.

A fifth embodiment of the optical fiber splicing method in accordance with the present invention will now be explained with reference to FIG. 7. The optical fiber splicing method in accordance with the fifth embodiment includes a splicing step (S501), a condition setting step (S502), an earlier heating step (S503), an earlier measuring step (S504), a change determining step (S505), a later heating step (S506), a later measuring step (S507), and a termination determining step (S508).

The splicing step (S501) is similar to S101 in the first embodiment. In its subsequent condition setting step (S502), a set value $\Delta\alpha_{01}$ used in the change determining step (S505), which will be carried out later, and a set value $\alpha_{02}$ used in the termination determining step (S508), which will be carried out later, are set. Here, $\Delta_{01} \geq \alpha_{02}$.

Then, the earlier heating step (S503), earlier measuring step (S504), and change determining step (S505) are repeatedly carried out until it is determined in the change determining step that a predetermined condition is satisfied. Thereafter, the later heating step (S506), later measuring step (S507), and termination determining step (S508) are repeatedly carried out until it is determined in the termination determining step that they should be terminated.

Each of the earlier heating step (S503) and later heating step (S506) is similar to S103 in the first embodiment. However, the heating temperature is lower or the heating time is shorter in the later heating step (S506) than in the earlier heating step (S503). It will also be preferred in the later heating step (S506) if the heating temperature is lower and the heating time is shorter.

Each of the earlier measuring step (S504) and later measuring step (S507) is similar to S104 in the first embodiment. The value of splice loss measured in the n-th measuring step (S504, S507) throughout the earlier and later steps is defined as $\alpha_n$.

In the change determining step (S505), the splice loss $\alpha_n$ measured immediately in the earlier measuring step (S504) immediately prior thereto and the set value $\alpha_{01}$ set in the condition setting step (S502) are compared with each other in terms of the magnitude, and it is determined whether the alternation of the earlier heating step (S503) and earlier measuring step (S504) should be terminated or not. If the splice loss $\alpha_n$ is not greater than the set value $\alpha_{01}$, then it is determined that the above-mentioned alternation should be terminated, whereby the flow proceeds to the subsequent later heating step (S506). If the splice loss $\alpha_n$ exceeds the set value $\alpha_{01}$, then the flow returns to the previous earlier heating step (S503) in order to continue the above-mentioned alternation.

The termination determining step (S508) is similar to S105 in the first embodiment. However, the splice loss $\alpha_n$ is compared with the set value $\alpha_{02}$ in terms of magnitude. If the splice loss $\alpha_n$ exceeds the set value $\alpha_{02}$, then the flow returns to the previous later heating step (S506).

As in the foregoing, the optical fiber splicing method in accordance with this embodiment fully reduces the splice loss at room temperature as with the optical fiber splicing method in accordance with the above-mentioned first embodiment.

In the optical fiber splicing method in accordance with this embodiment, the heating temperature is higher or the heating time is longer in the earlier heating step carried out until the splice loss becomes the set value $\alpha_{01}$ or less as compared with the later heating step, whereby the time required for the alternation of the earlier heating step (S503) and earlier measuring step (S504) is shortened. As a result, the total time required for the optical fiber connecting operation is shortened.

Specific Example 5 of the optical fiber splicing method in accordance with the fifth embodiment will now be explained. The optical fibers and arc discharge used in this example are the same as those in Example 1. The splice loss after the splicing step was 1.13 dB. A burner was used in each of the earlier and later heating steps. In the earlier heating step, a mixed gas composed of a propane gas (with a feed rate of 30 cc/min) and an oxygen gas (with a feed rate of 45 cc/min) was supplied to the burner. In the later heating step, a mixed gas composed of a propane gas (with a feed rate of 20 cc/min) and an oxygen gas (with a feed rate of 30 cc/min) was supplied to the burner. In each heating step, heating was carried out for 20 seconds. The time interval between one heating step and the next heating step was 10 seconds, during which the earlier measuring step and change determining step, or the later measuring step and termination determining step were carried out. The set value $\alpha_{01}$ was 0.50 dB, whereas the set value $\alpha_{02}$ was 0.20 dB.

The heating, measuring, and termination determining steps were repeatedly carried out 10 times until the measured splice loss $\alpha_n$ became the set value $\alpha_{01}$ or less. The splice loss $\alpha_{10}$ was 0.48 dB at the time when the change determining step was terminated. Thereafter, the later heating step, later measuring step, and termination determining step were repeatedly carried out 10 times until the measured splice loss $\alpha_n$ became the set value $\alpha_{02}$ or less. The splice loss $\alpha_{20}$ measured at the time when the number n of alternation throughout the earlier and later steps became 20 was 0.18 dB. The time required after terminating the condition setting step was 590 seconds.

Sixth Embodiment

Figure 8:
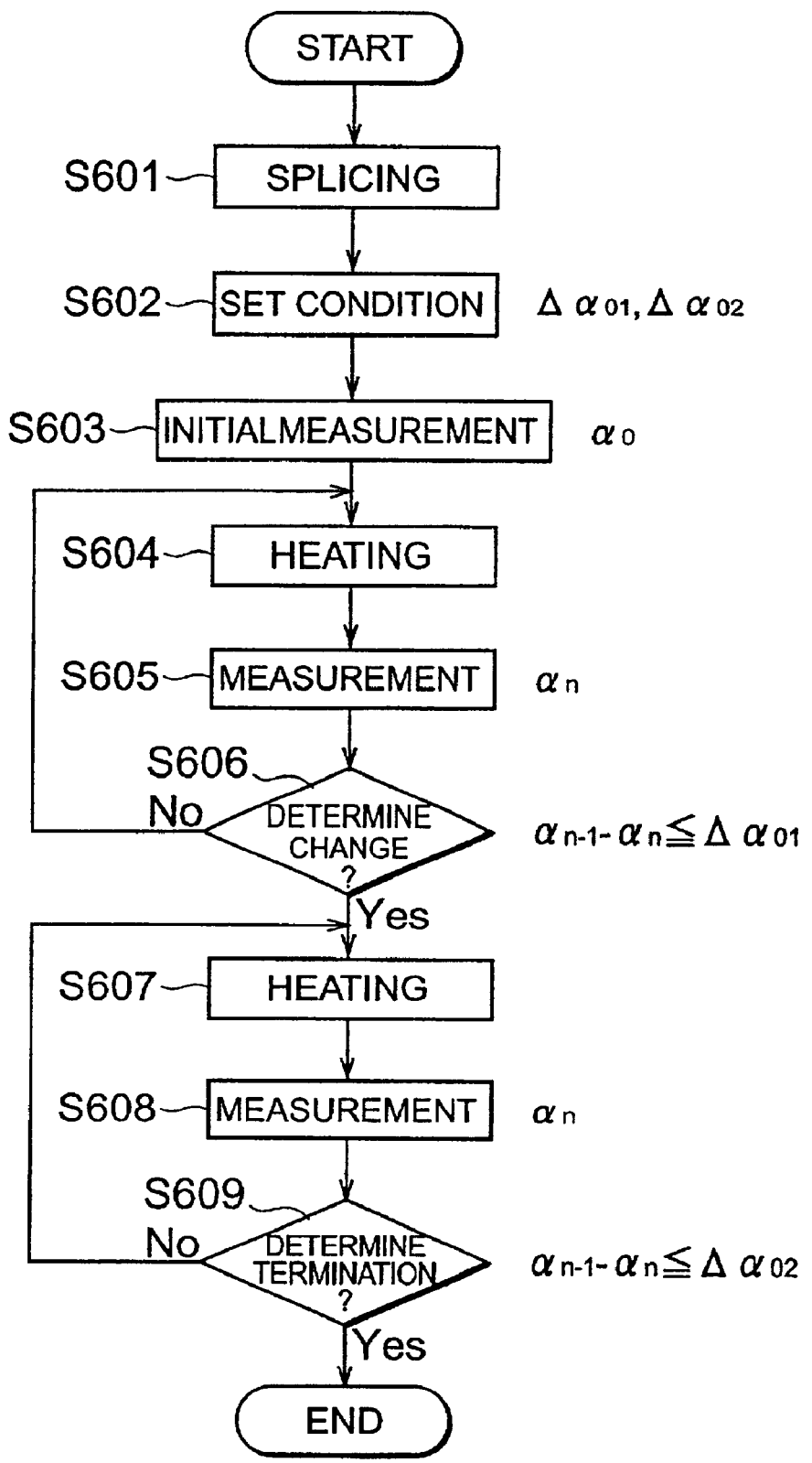
FIG. 8 is a flowchart for explaining the optical fiber splicing method in accordance with a sixth embodiment.

A sixth embodiment of the optical fiber splicing method in accordance with the present invention will now be explained with reference to FIG. 8. The optical fiber splicing method in accordance with the sixth embodiment includes a splicing step (S601), a condition setting step (S602), an initial measurement step (S603), an earlier heating step (S604), an earlier measuring step (S605), a change determining step (S606), a later heating step (S607), a later measuring step (S608), and a termination determining step (S609).

The heating step (S601) is similar to S101 in the first embodiment. In its subsequent condition setting step (S602), a set value $\Delta\alpha_{01}$ used in the change determining step (S606), which will be carried out later, and a set value $\Delta\alpha_{02}$ used in the change determining step (S609), which will be carried out later, are set. Here, $\Delta\alpha_{01} \geq \Delta\alpha_{02}$. The initial measurement step (S603) is similar to S203 in the second embodiment.

Thereafter, the earlier heating step (S604) through the termination determining step (S609) are repeatedly carried out as with the earlier heating step through the termination determining step in the fifth embodiment.

The earlier heating step (S604) and later heating step (S607) are similar to S503 and S506 in the fifth embodiment, respectively.

The earlier measuring step (S605) and later measuring step (S608) are similar to S504 and S507 in the fifth embodiment, respectively.

The change determining step (S606) is similar to S505 in the fifth embodiment. Here, the difference $\Delta\alpha_n$ $(=\alpha_{n-1}-\alpha_n)$ between the splice losses $\alpha_n$ and $\alpha_{n-1}$ is determined and, according to thus determined value and the set value $\Delta\alpha_{01}$, it is determined whether the alternation of the earlier heating step (S604) and earlier measuring step (S605) should be terminated or not. If the difference $\Delta\alpha_n$ is not greater than the set value $\Delta\alpha_{01}$, then it is determined that the above-mentioned alternation should be terminated, whereby the flow proceeds to the subsequent later heating step (S607) If the difference $\Delta\alpha_n$ exceeds the set value $\Delta\alpha_{01}$, then the flow returns to the previous earlier heating step (S604) in order to continue the above-mentioned alternation.

The termination determining step (S609) is similar to S508 in the fifth embodiment. Here, according to the value of difference $\Delta\alpha_n$ and the set value $\Delta\alpha_{02}$, it is determined whether the alternation of the later heating step (S607) and later measuring step (S608) should be terminated or not. If the difference $\Delta\alpha_n$ is not greater than the set value $\Delta\alpha_{02}$, then it is determined that the above-mentioned alternation should be terminated, whereby the optical fiber connecting operation is terminated. If the difference $\Delta\alpha_n$ exceeds the set value $\Delta\alpha_{02}$, then the flow returns to the previous later heating step (S607) in order to continue the above-mentioned alternation.

As in the foregoing, the optical fiber splicing method in accordance with this embodiment fully reduces the splice loss at room temperature as with the optical fiber splicing method in accordance with the above-mentioned second embodiment.

Also, the optical fiber splicing method in accordance with this embodiment shortens the time required for the alternation of the earlier heating step (S604) and earlier measuring step (S605) as with the fifth embodiment. As a result, the total time required for the optical fiber connecting operation is shortened.

Specific Example 6 of the optical fiber splicing method in accordance with the sixth embodiment will now be explained. The optical fibers, arc discharge, burner, mixed gas of the earlier heating step, and mixed gas of the later heating step used in this example are the same as those in Example 5. Heating was carried out for 20 seconds in each earlier heating step, and for 10 seconds in each later heating step. The time interval between one heating step and the next heating step was 10 seconds, during which the earlier measuring step, change determining step, later measuring step, or termination determining step was carried out. The set value $\Delta\alpha_{01}$ was 0.02 dB, whereas the set value $\Delta\alpha_{02}$ was 0.005 dB.

The earlier heating, earlier measuring, and change determining steps were repeatedly carried out 14 times until the difference $\Delta\alpha_n$ became the set value $\Delta\alpha_{01}$ or less. Thereafter, the later heating, later measuring, and termination determining steps were repeatedly carried out 7 times until the difference $\Delta\alpha_n$ became the set value $\Delta\alpha_{02}$ or less. The splice loss $\alpha_{21}$ measured at the time when the number n of alternation throughout the earlier and later steps became 21 was 0.18 dB. The time required after terminating the condition setting step was 550 seconds.

Seventh Embodiment

Figure 9:
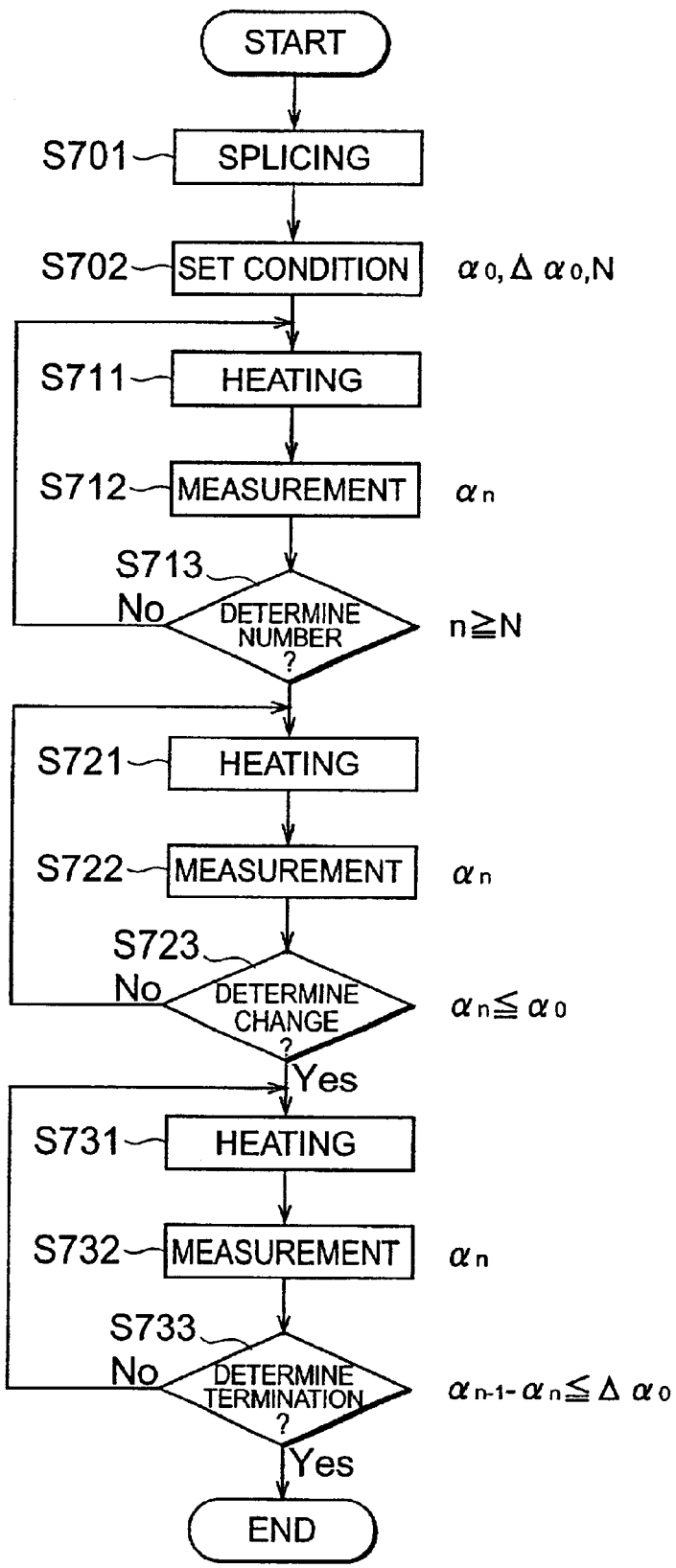
FIG. 9 is a flowchart for explaining the optical fiber splicing method in accordance with a seventh embodiment.

A seventh embodiment of the optical fiber splicing method in accordance with the present invention will now be explained with reference to FIG. 9. The optical fiber splicing method in accordance with the seventh embodiment includes a splicing step (S701), a condition setting step (S702), a heating step (S711), a measuring step (S712), a number determining step (S713), a heating step (S721), a measuring step (S722), a change determining step (S723), a heating step (S731), a measuring step (S732), and a termination determining step (S733).

The splicing step (S701) is similar to S101 in the first embodiment. In its subsequent condition setting step (S702), a set value N used in the number determining step (S713), which will be carried out later, a set value $\alpha_0$ used in the change determining step (S723), which will be carried out later, and a set value $\Delta\alpha_0$ used in the termination determining step (S733), which will be carried out later, are set.

Thereafter, the heating step (S711), measuring step (S712), and number determining step (S713) are repeatedly carried out until it is determined in the number determining step that a predetermined condition is satisfied. Subsequently, the heating step (S721), measuring step (S722), and change determining step (S723) are repeatedly carried out until it is determined in the change determining step that a predetermined condition is satisfied. Then, the heating step (S731), measuring step (S732), and termination determining step (S733) are repeatedly carried out until it is determined in the termination determining step that they should be terminated.

Though each of the heating steps (S711, S721, S731) is similar to S103 in the first embodiment, the heating temperature is lower or the heating time is shorter in the later heating step (S731) than in the earlier heating step (S721). It will also be preferred in the later heating step (S731) if the heating temperature is lower and the heating time is shorter.

Each of the measuring steps (S712, S722, S732) is similar to S104 in the first embodiment. The value of splice loss measured in the n-th measuring step (S712, S722, S732) throughout the operation is defined as $\alpha_n$.

In the number determining step (S713), it is determined whether the number n of alternation of the alternation of the heating step (S711) and measuring step (S712) has reached the set value N or not. If it is determined that the number n of alternation has reached the set value N, then the flow proceeds to the subsequent heating step (S721). If not, the flow returns to the previous heating step (S711).

The change determining step (S723) is similar to S505 in the fifth embodiment. Here, the splice loss $\alpha_n$ is compared with the set value $\alpha_0$ in terms of magnitude.

The termination determining step (S733) is similar to S206 in the second embodiment.

As in the foregoing, the optical fiber splicing method in accordance with this embodiment fully reduces the splice loss at room temperature as with the optical fiber splicing method in accordance with the above-mentioned third embodiment.

The optical fiber splicing method in accordance with this embodiment shortens the time required for the alternation of the earlier heating step (S721) and earlier measuring step (S722) as with the fifth embodiment. As a result, the total time required for the optical fiber connecting operation is also shortened.

Specific Example 7 of the optical fiber splicing method in accordance with the seventh embodiment will now be explained. The optical fibers and burner used in this embodiment are the same as those in Example 1. In S711 and S721, a mixed gas composed of a propane gas (with a feed rate of 30 cc/min) and an oxygen gas (with a feed rate of 45 cc/min) was supplied to the burner. In S731, a mixed gas composed of a propane gas (with a feed rate of 20 cc/min) and an oxygen gas (with a feed rate of 30 cc/min) was supplied to the burner. Heating was carried out for 20 seconds each in S711, and for 10 seconds each in S721 and S731. The time interval between one heating step and the next heating step was 10 seconds, during which S712 and S713, S722 and S723, or S732 and S733 were carried out. The set value N was 5, the set value $\alpha_0$ was 0.50 dB, whereas the set value $\Delta\alpha_0$ was 0.005 dB.

The earlier heating step, earlier measuring step, and change determining step were repeatedly carried out 15 times until the splice loss $\alpha_n$ became the set value $\alpha_0$ or less. Thereafter, the later heating step, later measuring step, and termination determining step were repeatedly carried out 6 times until the difference $\Delta\alpha_n$ became the set value $\Delta\alpha_0$ or less. The splice loss $\alpha_{21}$ measured at the time when the number n of alternation throughout the earlier and later stages became 21 was 0.19 dB. The time required after terminating the condition setting step was 570 seconds.

Eighth Embodiment

Figure 10:
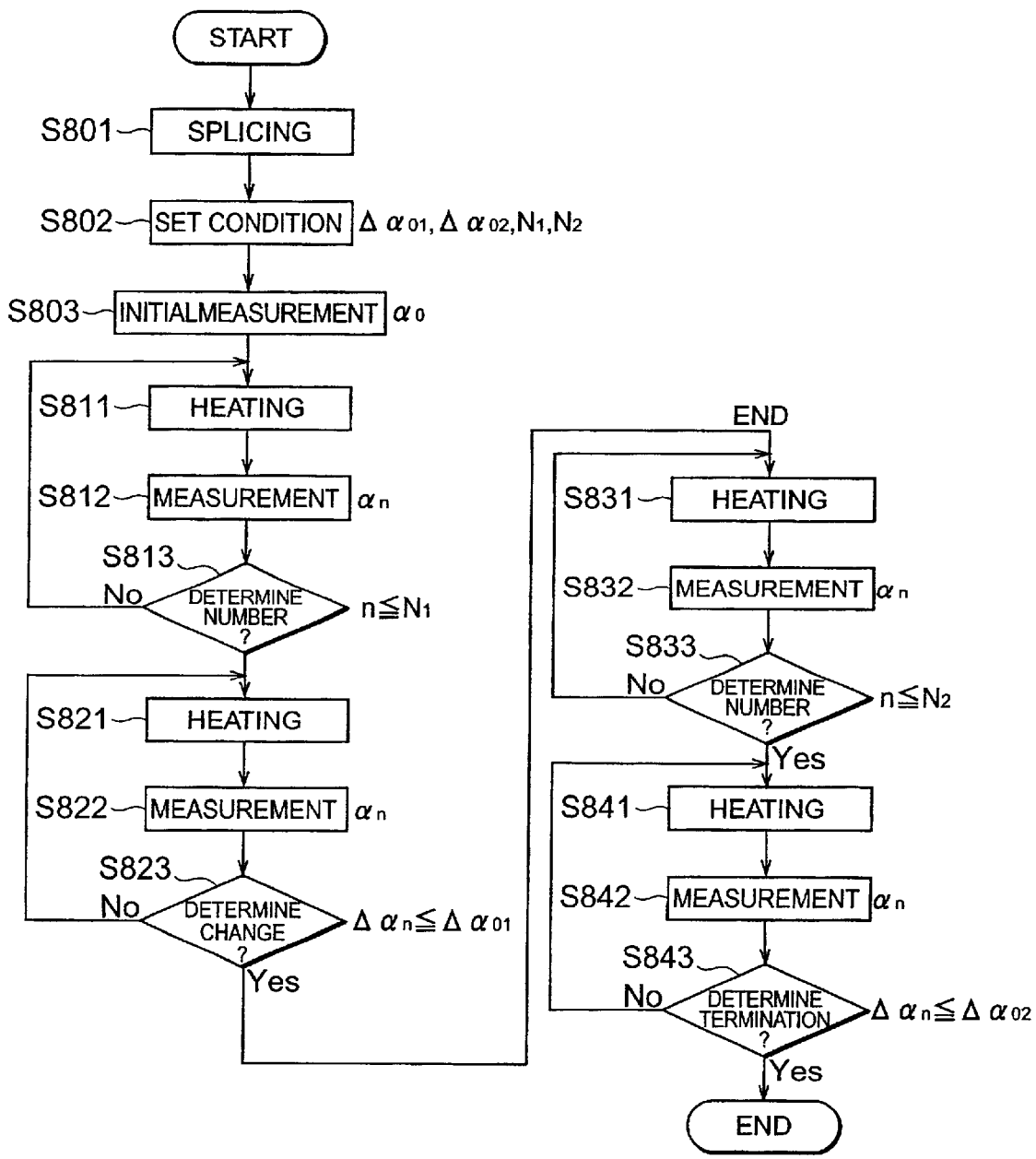
FIG. 10 is a flowchart for explaining the optical fiber splicing method in accordance with an eighth embodiment.

An eighth embodiment of the optical fiber splicing method in accordance with the present invention will now be explained with reference to FIG. 10. The optical fiber splicing method in accordance with the eighth embodiment includes a splicing step (S801), a condition setting step (S802), an initial measurement step (S803), a heating step (S811), a measuring step (S812), a number determining step (S813), a heating step (S821), a measuring step (S822), a change determining step (S823), a heating step (S831), a measuring step (S832), a number determining step (S833), a heating step (S841), a measuring step (S842), and a termination determining step (S843).

The splicing step (S801) is similar to S101 in the first embodiment. In its subsequent condition setting step (S802), a set value $N_1$ used in the number determining step (S813), which will be carried out later, a set value $\Delta\alpha_{01}$ used in the change determining step (S823), which will be carried out later, a set value $N_2$ used in the number determining step (S833), which will be carried out later, and a set value $\Delta\alpha_{02}$ used in the change determining step (S843), which will be carried out later, are set. Here, $\Delta\alpha_{01} \geq \Delta\alpha_{02}$, and $N_1 < N_2$. The initial measurement step (S803) is similar to S203 in the second embodiment.

The subsequent heating step (S811) through the change determining step (S823) are similar to S711 through S723 in the seventh embodiment.

Subsequently, the heating step (S831), measuring step (S832), and number determining step (S833) are repeatedly carried out until it is determined in the number determining step (S833) that a predetermined condition is satisfied. Also, the heating step (S841), measuring step (S842), and change determining step (S843) are repeatedly carried out until it is determined in the termination determining step (S843) that a predetermined condition is satisfied.

Each of the heating steps (S811, S821, S831, S841) is similar to S103 in the first embodiment. The heating temperature is lower or the heating time is shorter in the later heating steps (S831, S841) than in the earlier heating steps (S811, S821). It will also be preferred in the later heating steps (S831, S841) if the heating temperature is lower and the heating time is shorter.

Each of the measuring steps (S812, S822, S832, S842) is similar to S104 in the first embodiment. The n-th measurement step (S812, S822, S832, S842) throughout the operation is defined as $\alpha_n$.

The number determining step (S813) is similar to S713 in the seventh embodiment. Here, it is determined whether the number n of alternation has reached $N_1$ or not.

The change determining step (S823) is similar to S606 in the sixth embodiment.

In the number determining step (S833), it is determined whether the number n of alternation of alternation of the heating steps (S811, S821, S831) and measuring steps (S812, S822, S832) in total has reached $N_2$ or not. If it is determined that the total number n of alternation has reached $N_2$, then the flow proceeds to the subsequent heating step (S841). If not, the flow returns to the previous heating step (S831).

The termination determining step (S843) is similar to S609 in the sixth embodiment.

As in the foregoing, the optical fiber splicing method in accordance with this embodiment fully reduces the splice loss at room temperature as with the optical fiber splicing method in accordance with the above-mentioned second embodiment.

The optical fiber splicing method in accordance with this embodiment shortens the time required for the alternation of the earlier heating steps (S811, S821) and measuring steps (S812, 822) as with the fifth embodiment. As a result, the total time required for the optical fiber connecting operation is also shortened.

Since the number determining steps (S813, S833) are provided, the optical fiber splicing method in accordance with this embodiment fully reduces the splice loss at room temperature as with the third embodiment.

Specific Example 8 of the optical fiber splicing method in accordance with the eighth embodiment will now be explained. The optical fibers, arc discharge, and burner used in this example are the same as those in Example 1. In the earlier heating steps (S811, S821), a mixed gas composed of a propane gas (with a feed rate of 25 cc/min) and an oxygen gas (with a feed rate of 36 cc/min) was supplied to the burner. In the later heating steps (S831, S841), a mixed gas composed of a propane gas (with a feed rate of 20 cc/min) and an oxygen gas (with a feed rate of 30 cc/min) was supplied to the burner. The heating time in each heating step and the time interval between one heating step and the next heating step were the same as those in Example 7. The set value $\Delta\alpha_{01}$ was 0.02 dB, whereas the set value $\Delta\alpha_{02}$ was 0.005 dB. The set value $N_1$ was 5, whereas the set value $N_2$ was 16.

The alternation of the heating steps (S811, S821) and measuring steps (S812, S822) was repeatedly carried out 10 times until the difference $\alpha_n$ became the set value $\Delta\alpha_{01}$ or less. Thereafter, the alternation of the heating steps (S831, S841) and measuring steps (S832, S842) was repeatedly carried out 13 times until the difference $\alpha_n$ became the set value $\Delta\alpha_{02}$ or less. The splice loss $\alpha_{23}$ measured at the time when the total number n of alternation became 23 was 0.18 dB. The time required after terminating the condition setting step was 680 seconds.

Ninth Embodiment

Figure 11:
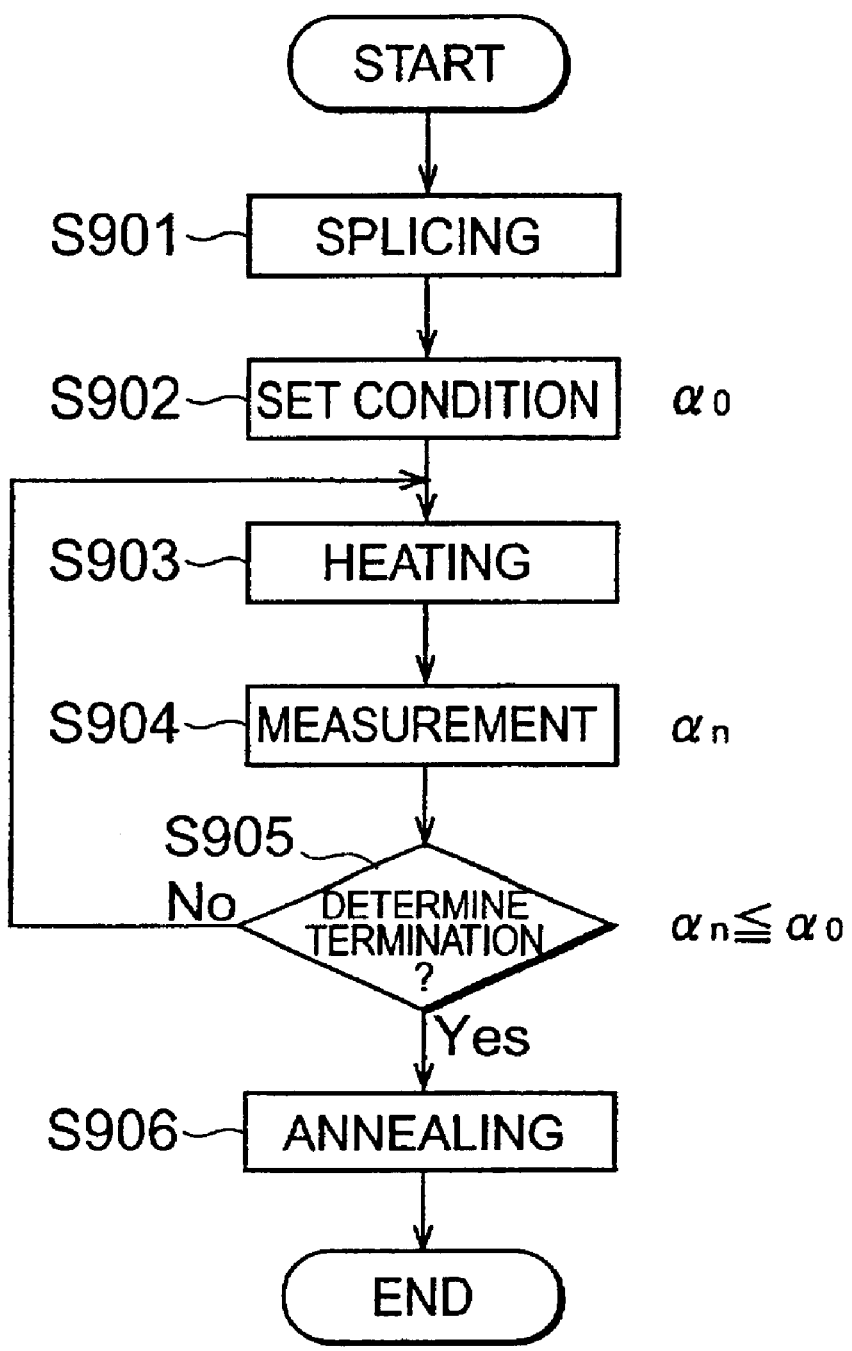
FIG. 11 is a flowchart for explaining the optical fiber splicing method in accordance with a ninth embodiment.

A ninth embodiment of the optical fiber splicing method in accordance with the present invention will now be explained with reference to FIG. 11. The optical fiber splicing method in accordance with the ninth embodiment includes a splicing step (S901), a condition setting step (S902), a heating step (S903), a measuring step (S904), a termination determining step (S905), and an annealing step (S906).

The splicing step (S901) though the termination determining step (S905) are carried out as in the first embodiment. If the splice loss $\alpha_n$ is not greater than the set value $\alpha_0$, then the flow proceeds to the subsequent annealing step. If the splice loss $\alpha_n$ exceeds the set value $\alpha_0$, then the flow returns to the previous heating step (S903) In the annealing step, the vicinity of the fusion-spliced part is heated at an initial temperature of at least 500° C. but not higher than 1500° C. and then is slowly cooled to 200° C. over a period of at least 10 seconds.

In this annealing step, the fusion-spliced part A is cooled from a predetermined initial temperature to a temperature of 200° C. over a predetermined period or longer. In the annealing step, the cooling rate from the initial temperature to 200° C. may be either constant or inconstant. For example, the cooling rate may be set higher at first and gradually slowed down.

Figure 12A:
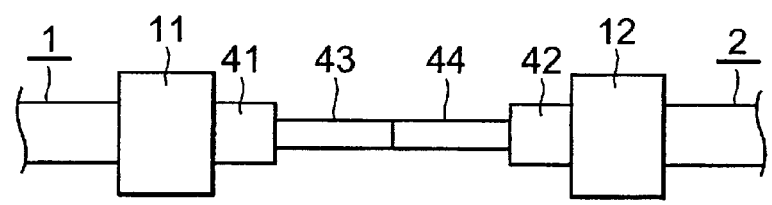
FIG. 12A is a view showing a state where optical fibers are fused together.
Figure 12B:
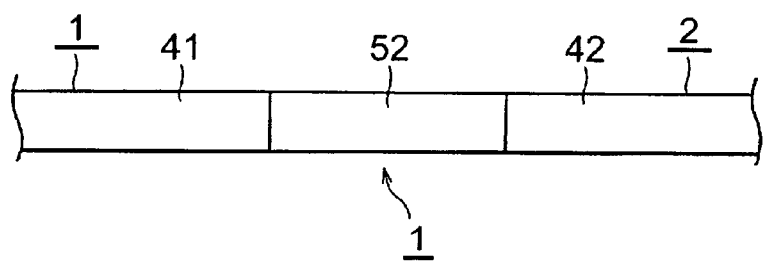
FIG. 12B is a view showing a state where exposed glass fibers are re-coated with a resin.

FIG. 12A is a view showing a state where optical fibers 1, 2 are fused together. After the cooling, as shown in FIG. 12B, exposed glass fibers 43, 44 are re-coated with a resin 52. The outer diameter of the coating with the resin 52 is substantially equal to the outer diameter of each of the coatings formed by resins 41, 42 about the optical fibers 1, 2, respectively. Thereafter, the optical fibers 1, 2 including the fusion-spliced part A is subjected to a predetermined packaging process, e.g., wound about a bobbin, whereby the connecting of optical fibers is completed.

Since the thermal distortion generated in the splicing step (and heating step) is eliminated in the annealing step, mechanical strength is fully secured in a region including the fusion-spliced part A, whereby thus spliced optical fiber device 1 is not required to be reinforced with steel wires.

Specific Example 9 of the optical fiber splicing method in accordance with the ninth embodiment will now be explained. This example was the same as the example concerning the first embodiment until the end of the termination determining step.

In the annealing step, while a mixed gas composed of a propane gas (with a feed rate of 20 cc/min) and an oxygen gas (with a feed rate of 30 cc/min) was flowing, the propane gas was burnt, so as to form a flame, by which the optical fiber was reheated. The temperature of flame was 1500° C., and the optical fiber was annealed while the temperature was gradually lowered to 200° C. Some samples were prepared while variously changing the time required for annealing.

Figure 13:
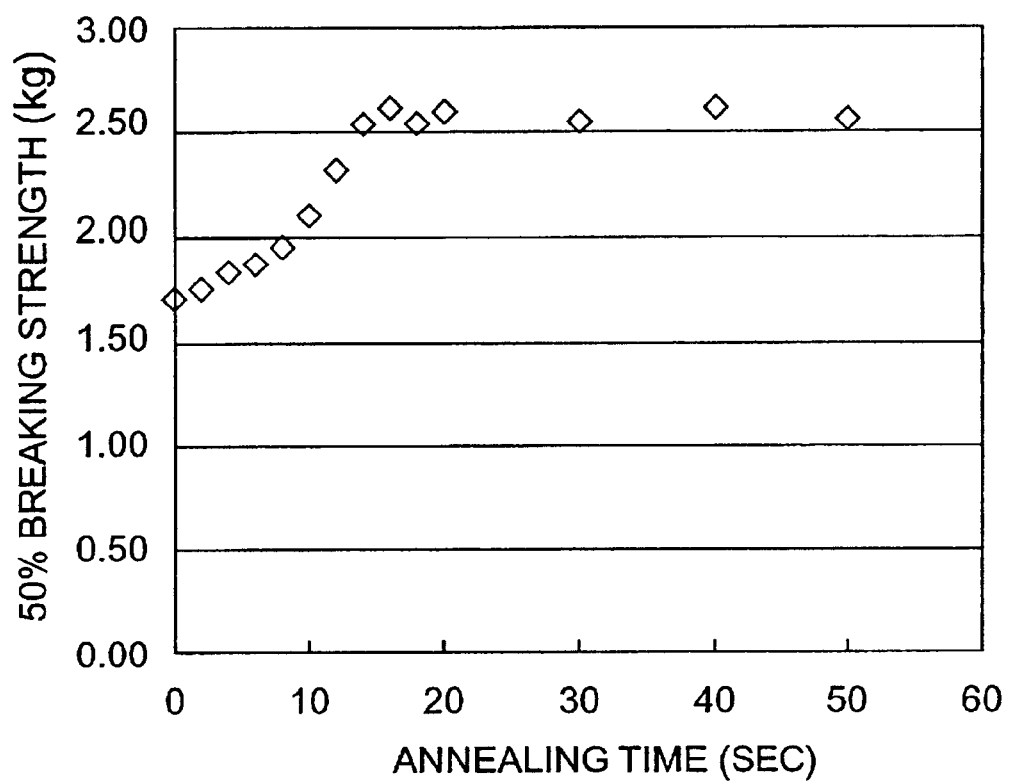
FIG. 13 is a graph showing the relationship between annealing time and 50% breaking strength in Example 9.

Then, each sample was subjected to a breaking test at a gauge length of 200 mm and a pulling rate of 5 mm/min, whereby the 50% breaking strength was measured. FIG. 13 is a graph showing the relationship between annealing time and 50% breaking strength in Example 9. As can be seen from this graph, a favorable optical fiber having a 50% breaking strength of 19.6 N (2.00 kg) or greater is obtained when the annealing time in the annealing step is at least 10 seconds. When the annealing time in the annealing step is 14 seconds or longer, a more favorable optical fiber having a 50% breaking strength of 24.5 N (2.50 kg) or greater can be obtained.

No change in loss has been seen due to the addition of annealing step. This is presumed to be because of the fact that the amount of dispersion of fiber dopant caused by the thermal history in the annealing step is quite small.

Tenth Embodiment

Figure 14:
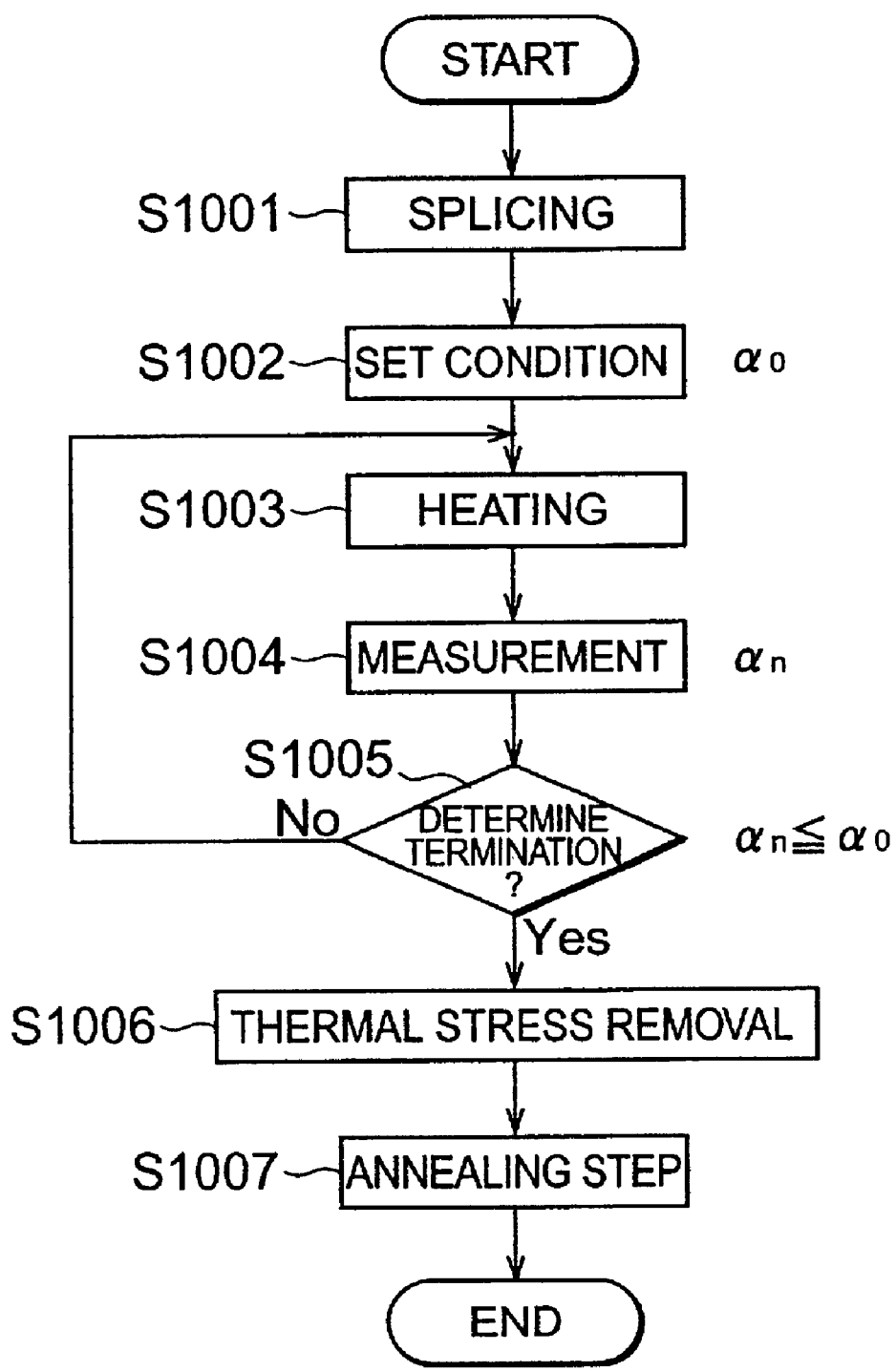
FIG. 14 is a flowchart for explaining the optical fiber splicing method in accordance with a tenth embodiment.

A tenth embodiment of the optical fiber splicing method in accordance with the present invention will now be explained with reference to FIG. 14. The optical fiber splicing method in accordance with the tenth embodiment includes a splicing step (S1001), a condition setting step (S1002), a heating step (S1003), a measuring step (S1004), a termination determining step (S1005), a thermal stress removal step (S1006), and an annealing step (S1007).

The splicing step (S1001) through the termination determining step (S1005) are carried out as in the first embodiment. If the splice loss $\Delta\alpha_n$ is not greater than the set value $\alpha_0$ in the termination determining step, then the flow proceeds to the subsequent thermal stress removal step. If the splice loss $\alpha_n$ exceeds the set value $\alpha_0$, then the flow returns to the previous heating step (S1003).

The heating temperature range in the thermal stress removal step is not higher than the softening temperature of glass fibers 43, 44 but is sufficient for eliminating thermal distortions, and is at least 500° C. but not higher than 1500° C. Preferably, it is at least 500° C. but not higher than 1200° C. The heating time in the thermal stress removal step is shorter than the total heating time in the heating step, whereby a short time on the order of several seconds to several ten seconds is sufficient therefor. The heat treatment in the thermal stress removal step eliminates thermal distortions generated about the fusion-spliced part in the splicing step or heating step, thereby restoring the mechanical strength in the vicinity of the fusion-spliced part.

Preferably, in the thermal stress removal step, a region including the fusion-spliced part is heat-treated while a heating source is relatively moved in a longitudinal direction of the glass fibers 43, 44. As a consequence, thermal distortions in the area heated in the fusing or heating step can be eliminated in the thermal stress removal step. Since the temperature in the thermal stress removal step is relatively low, the range heated by a fixed heating source (e.g., about 5 mm to 10 mm) is narrower than the range heated in the thermal stress removal step (i.e., the range where thermal distortions occur, e.g., about 10 mm to 15 mm). Preferably, the longitudinal temperature gradient of two optical fibers in the thermal stress removal step is 500° C./mm or lower. When the temperature gradient is made smaller as such, thermal distortions are fully eliminated.

The annealing step after the thermal stress removal step is similar to that in the ninth embodiment.

Figure 15:
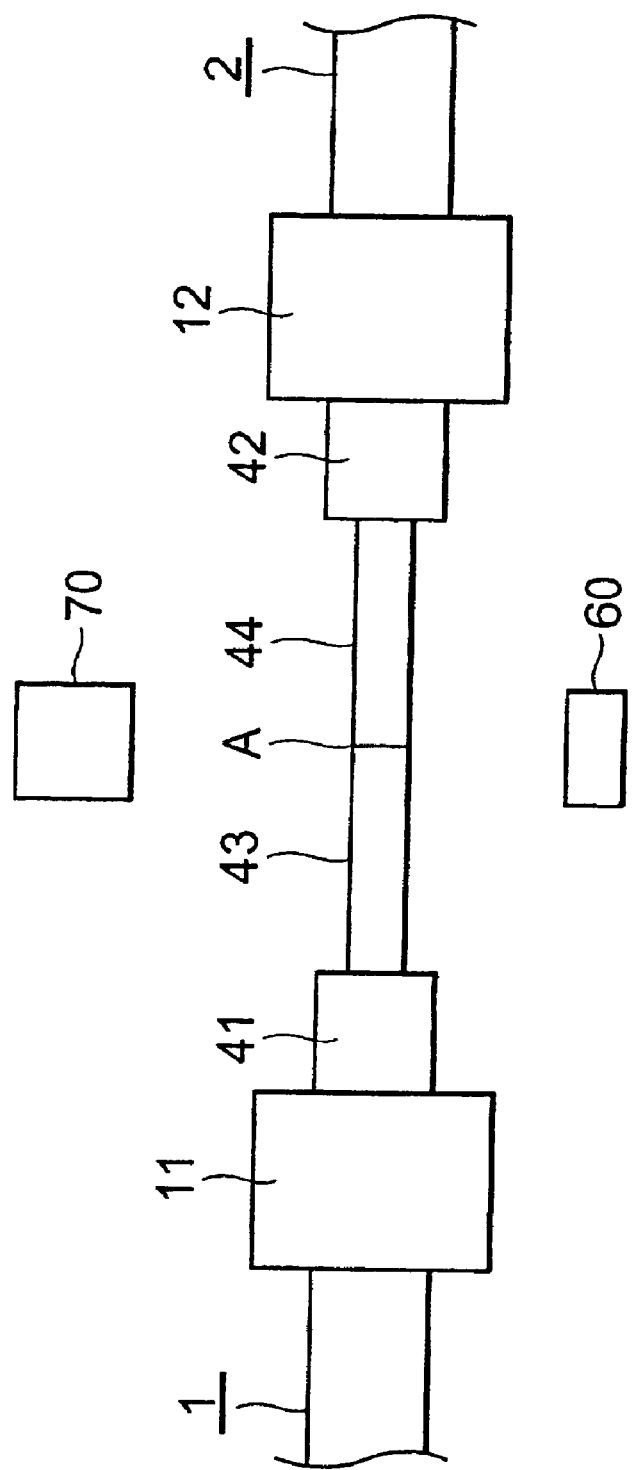
FIG. 15 is a diagram of an apparatus for carrying out heat treatments in the thermal stress removal step and annealing step.

FIG. 15 is a diagram showing an apparatus for carrying out heat treatments in the thermal stress removal step and annealing step in the optical fiber splicing methods in accordance with the ninth and tenth embodiments. As depicted, a heating source 60 for heating the fusion-spliced part A and its surroundings, and a radiation thermometer 70 for measuring the temperature of the fusion-spliced part A and its surroundings are disposed near the fusion-spliced part A. The temperature of the fused part A and its surroundings is measured by the radiation thermometer 70, and the heating of the fusion-spliced part A and its surrounding by the heating source 60 is controlled such that the temperature measured by the radiation thermometer 70 becomes an appropriate value.

The heating source 60 is an electrode for arc discharge, a burner, or a heater (electric heater, ceramic heater, or the like), and can move back and forth in longitudinal directions of the glass fibers 43, 44. Upon heating with the burner, a flammable gas (e.g., a hydrocarbon gas such as propane gas) and an oxygen gas are supplied to the burner, so as to generate a flame, by which the fusion-spliced part A and its surroundings are heat-treated. Using arc discharge as the heating source 60 is favorable in that a fusion-splicing apparatus can be employed as it is. Using a burner as the heating source is favorable in that the fusion-spliced part A and its surroundings can be heated with a distribution, and in that the heating source can be made smaller. Using a heater as the heating source 60 is favorable in that the fusion-spliced part A and its surroundings can be heated with a distribution, and in that the heating atmosphere is clean.

The radiation temperature 70 is a combination of a two-dimensional infrared radiation thermometer and a magnifying lens, and measures the temperature distribution of the fusion-spliced part A and its surroundings with the two-dimensional infrared radiation thermometer through the magnifying lens. In view of the form and material of the glass fibers 43, 44 to be measured, the emissivity is set to 0.5. In each of the dopant difsplicing step and thermal stress removal step, the heating source 60 is arranged or longitudinally moved such that the temperature distribution measured by the radiation thermometer 70 attains the highest temperature at the fusion-spliced part A or in close proximity thereto, and this highest temperature is employed as the heating temperature in each step.

In the annealing step, the heating source 60 is arranged such that the temperature distribution measured by the radiation thermometer 70 attains the highest temperature at the fusion-spliced part A or in close proximity thereto, and the heating source 60 is controlled such that the descending rate of the highest temperature falls within the above-mentioned predetermined range.

Specific Example 10 of the optical fiber splicing method in accordance with the tenth embodiment will now be explained. This example was the same as the example in accordance with the first embodiment until the end of the termination determining step.

Figure 16:
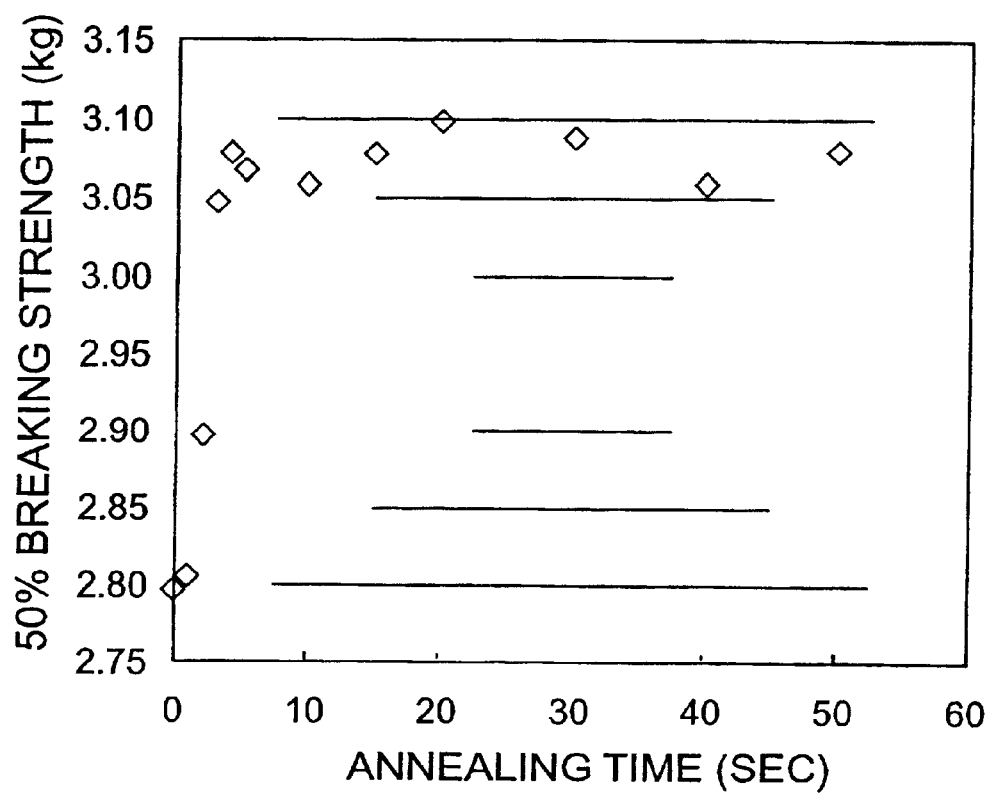
FIG. 16 is a graph showing the relationship between annealing time and 50% breaking strength in the tenth embodiment.

In the subsequent thermal stress removal step, the fusion-spliced part A and its surroundings were heated for 30 seconds at a temperature of 700° C., so as to reduce thermal distortions about the fusion-spliced part A. In its subsequent annealing step, the amount of gas supplied to the burner after the thermal stress removal step is mildly lowered, so as to anneal the fusion-spliced part A from the heating temperature (initial temperature) of 700° C. in the thermal stress removal step to a temperature of 200° C. Some samples were prepared while variously changing the time required for annealing from an initial temperature of 1500° C. to a temperature of 200° C. in the annealing step. Each sample was subjected to a breaking test with a gauge length of 200 mm and a pulling rate of 5 mm/min, so as to measure its 50% breaking strength. FIG. 16 is a graph showing the relationship between annealing time and 50% breaking strength in Example 10. As can be seen from this graph, the 50% breaking strength was at least 28.42 N (2.90 kg) and at least 29.4 N (3.00 kg) when the annealing time in the annealing step was at least 2 seconds and at least 3 seconds, respectively, whereby favorable results were obtained.

No change in loss has been seen due to the addition of annealing step. This is presumed to be because of the fact that the amount of dispersion of fiber dopant caused by the thermal history in the annealing step is quite small.

Comparative Example

A comparative example of the optical fiber splicing method will now be explained. The optical fibers, arc discharge, and burner used in the comparative example are the same as those in each of the above-mentioned examples. In the heating step, a mixed gas composed of a propane gas (with a feed rate of 20 cc/min) and an oxygen gas (with a feed rate of 30 cc/min) was supplied to the burner, and the splice loss was measured during the heating. The heating step was terminated at the time when thus measured splice loss was the lowest. The splice loss measured after terminating the heating was 0.25 dB, whereas the time required for the heating step was 900 seconds.

Also, when a mixed gas of a propane gas (with a feed rate of 30 cc/min) and an oxygen gas (with a feed rate of 45 cc/min) was supplied to the burner, the splice loss was measured during the heating, and the heating step was terminated at the time when thus measured splice loss was the lowest. In this case, the splice loss measured after terminating the heating was 0.30 dB, whereas the time required for the heating step was 540 seconds.

As can be seen when each example and the comparative example are compared with each other, the splice loss was 0.25 dB or 0.30 dB in the comparative example, whereas that in each example was low, i.e., 0.17 to 0.20 dB. Thus, in the embodiments of the present invention, heating and measuring steps are alternately carried out, whereas the alternation is terminated according to the splice loss measured when each optical fiber is not heated, whereby the splice loss at room temperature is fully reduced.

Modified Examples

Without being restricted to the above-mentioned embodiments, the present invention can be modified in various manners. For example, heating conditions (temperature and time) in heating steps may be changed a plurality of times. As for values such as N, $\alpha_0$, and $\Delta\alpha_0$ used for determining changes and terminations, both or one of the upper and lower limits may be defined. These cases are suitable when changes in splice loss with respect to the number of heating operations are more complicated.

Though the ninth embodiment relates to an optical fiber splicing method in which an annealing step is added to the optical fiber splicing method in accordance with the first embodiment, and the tenth embodiment relates to an optical fiber splicing method in which a thermal stress removal step and an annealing step are added to the optical fiber splicing method in accordance with the first embodiment, the annealing step or distortion eliminating step may also be added to any of the second to eighth embodiment.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An optical fiber splicing method of a first optical fiber and a second optical fiber to each other by fusing respective end faces thereof, said method comprising:

a splicing step of fusing said respective end faces of said first and second optical fibers and splicing them;

a heating step of heating a region including a fusion-spliced part between said first and second optical fibers fused in said splicing step;

a measuring step, alternately carried out with said heating step, of measuring a splice loss between said first and second optical fibers fused in said splicing step; and a termination determining step of determining, according to a splice loss value measured in said measuring step, whether or not to terminate alternation of said heating and measuring steps;

wherein said alternation is terminated when it is determined in said termination determining step that said alternation should be terminated.

2. An optical fiber splicing method according to claim 1, further comprising a change determining step of determining, according to said splice loss value measured in said measuring step, whether or not to change a heating condition in said heating step thereafter;

wherein said heating condition in said heating step thereafter is changed when it is determined in said change determining step that said heating condition should be changed.

3. An optical fiber splicing method according to claim 2, wherein, when it is determined in said change determining step that said heating condition should be changed, a heating time is shortened in said heating step thereafter.

4. An optical fiber splicing method according to claim 2, wherein, when it is determined in said change determining step that said heating condition should be changed, a heating temperature is lowered while a heating time is shortened in said heating step thereafter.

5. An optical fiber splicing method according to claim 2, further comprising an annealing step of cooling a fusion-spliced part to a temperature of 200° C. over a period of at least 10 seconds after it is determined in said termination determining step that said alternation of said heating and measuring steps should be terminated and thus is terminated.

6. An optical fiber splicing method according to claim 2, further comprising a thermal stress removal step of eliminating a thermal distortion by heat-treating a region including a fusion-spliced part at a predetermined temperature of at least 500° C. but not higher than 1500° C. while being lower than the heating temperature in said heating step after it is determined in said termination determining step that said alternation of said heating and measuring steps should be terminated and thus is terminated; and an annealing step of cooling said fusion-spliced part from said predetermined temperature to a temperature of 200° C. over a period of at least 2 seconds after said thermal stress removal step.

7. An optical fiber splicing method according to claim 2, wherein it is determined in said change determining step that said heating condition should be changed if said splice loss measured in said measuring step is a set value or less.

8. An optical fiber splicing method according to claim 2, wherein it is determined in said change determining step that said heating condition should be changed if the difference between said splice loss measured in said measuring step and that at a previous measuring time becomes a set value or smaller.

9. An optical fiber splicing method according to claim 2, wherein said change determining step is performed within a range of only a predetermined number of the alternation.

10. An optical fiber splicing method according to claim 2, including a plurality of change determining steps.

11. An optical fiber splicing method according to claim 2, wherein, when it is determined in said change determining step that said heating condition should be changed, a heating temperature is lowered in said heating step thereafter.

12. An optical fiber splicing method according to claim 1, further comprising an annealing step of cooling a fusion-spliced part to a temperature of 200° C. over a period of at least 10 seconds after it is determined in said termination determining step that said alternation of said heating and measuring steps should be terminated and thus is terminated.

13. An optical fiber splicing method according to claim 12, wherein a region including said fusion-spliced part is heat-treated in said annealing step.

14. An optical fiber splicing method according to claim 1, further comprising a thermal stress removal step of eliminating a thermal distortion by heat-treating a region including a fusion-spliced part at a predetermined temperature of at least 500° C. but not higher than 1500° C. while being lower than the heating temperature in said heating step after it is determined in said termination determining step that said alternation of said heating and measuring steps should be terminated and thus is terminated; and an annealing step of cooling said fusion-spliced part from said predetermined temperature to a temperature of 200° C. over a period of at least 2 seconds after said thermal stress removal step.

15. An optical fiber splicing method according to claim 14, wherein a region including said fusion-spliced part is heat-treated in said thermal stress removal step while a heating source is relatively moved in a longitudinal direction of said two optical fibers.

16. An optical fiber splicing method according to claim 14, wherein said two optical fibers have a longitudinal temperature gradient of 500° C./mm or less in said thermal stress removal step.

17. An optical fiber splicing method according to claim 1, wherein it is determined in said termination determining step that said alternation should be terminated if said splice loss measured in said measuring step becomes a set value or less.

18. An optical fiber splicing method according to claim 1, wherein it is determined in said termination determining step that said alternation should be terminated if the difference between said splice loss measured in said measuring step and that at a previous measuring time becomes a set value or smaller.

19. An optical fiber splicing method according to claim 1, wherein said termination determining step is performed within a range of only a predetermined number of the alternation.

20. An optical fiber splicing method according to claim 1, wherein the heating time in the first heating step is longer than that in the second and later heating steps.

21. An optical fiber spliced by the optical fiber splicing method according to claim 1.

* * * * *